United States Patent [19]

Harms et al.

[11] Patent Number: 5,042,982
[45] Date of Patent: Aug. 27, 1991

[54] POSITIONING DEVICE

[76] Inventors: Jürgen Harms, Belchenweg 9, D;
Lutz Biedermann,
Berta-Suttner-Strasse 23, D-7730
VS-Schwenningen, both of Fed.
Rep. of Germany

[21] Appl. No.: 328,073
[22] PCT Filed: Jul. 8, 1988
[86] PCT No.: PCT/EP88/00617
§ 371 Date: Feb. 21, 1989
§ 102(e) Date: Feb. 21, 1989
[87] PCT Pub. No.: WO89/00028
PCT Pub. Date: Jan. 12, 1989

[30] Foreign Application Priority Data

Jul. 8, 1987 [DE] Fed. Rep. of Germany ....... 3722590
Jan. 4, 1988 [DE] Fed. Rep. of Germany ....... 3800052

[51] Int. Cl.⁵ .............................. A61F 5/04; A61F 5/00
[52] U.S. Cl. ........................................ 606/61; 128/69
[58] Field of Search .............. 128/69, 92 R, 92 Z,
128/92 YM, 92 YL; 606/60, 61, 73, 90

[56] References Cited

U.S. PATENT DOCUMENTS

| 4,041,939 | 8/1977 | Hall | 128/69 |
| 4,274,401 | 6/1981 | Miskew | 128/92 YM |
| 4,611,580 | 9/1986 | Wu | 128/69 |
| 4,611,582 | 9/1986 | Duff | 128/69 |
| 4,658,809 | 4/1987 | Ulrich et al. | 128/92 YM |

FOREIGN PATENT DOCUMENTS 2649042 1/1978 Fed. Rep. of Germany ........ 128/69
0210466 7/1986 Fed. Rep. of Germany .

Primary Examiner—Robert A. Hafer
Assistant Examiner—Michael Brown
Attorney, Agent, or Firm—Donald Brown

[57] ABSTRACT

A positioning means for stabilizing segments of the spinal column or dummies between two such segments has a simple design and allows a certain alignment of the connecting rods to be connected thereto. To this end a positioning screw (1) is provided which comprises a threaded shaft part (2) and a receiver part (3) for a rod (5) provided at the head side. The rod and the receiver part are rigidly connectable with each other by means of two nuts (6, 7; 18, 19; 20, 21). The respective part of the receiver part (3) forming the abutment for the nuts (6, 7) or for the intermediate members (6',7'; 16, 17) is formed as a spherical or cylindrical segment. The part which has to be brought in engagement with this segment comprises an inner surface which is formed as a hollow sphere or a hollow cylinder and which is concentric to the central axis of the nut or the intermediate piece, resp.

15 Claims, 3 Drawing Sheets

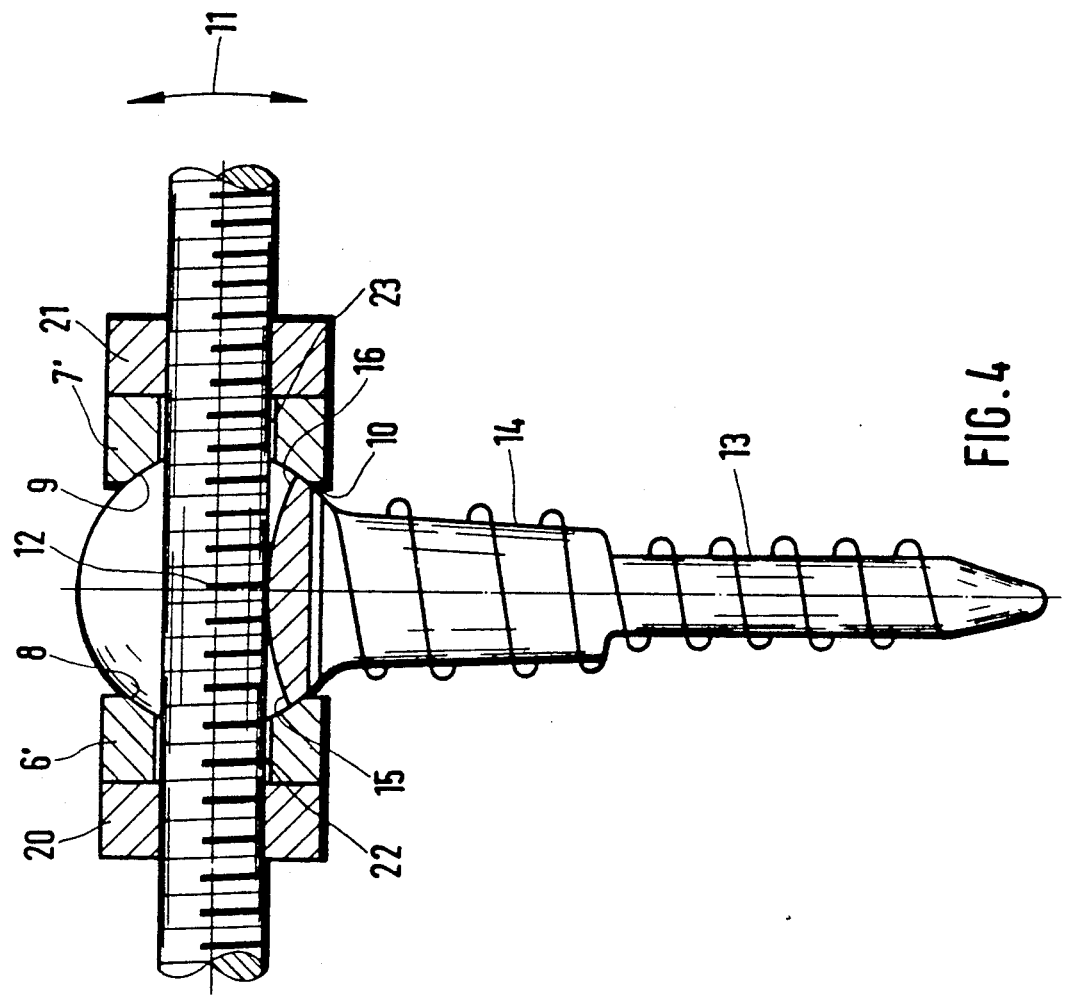
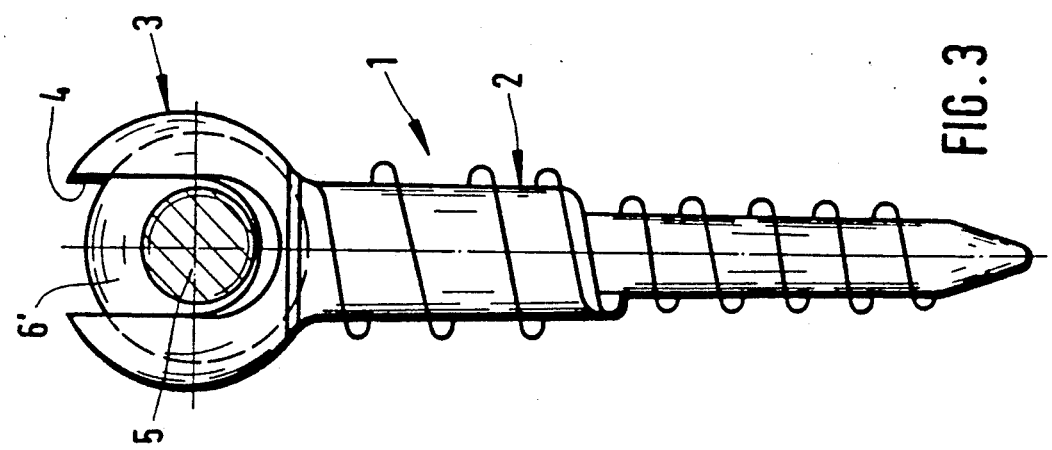

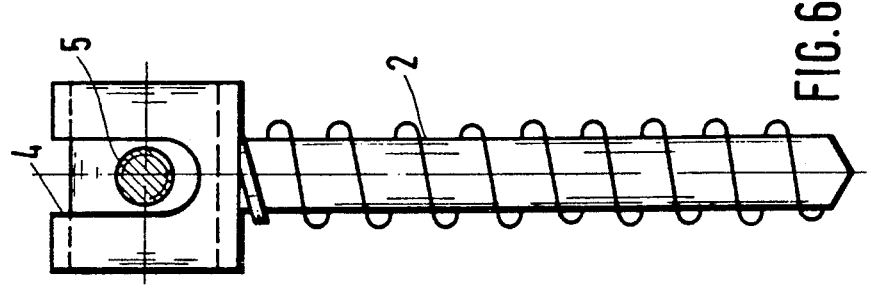
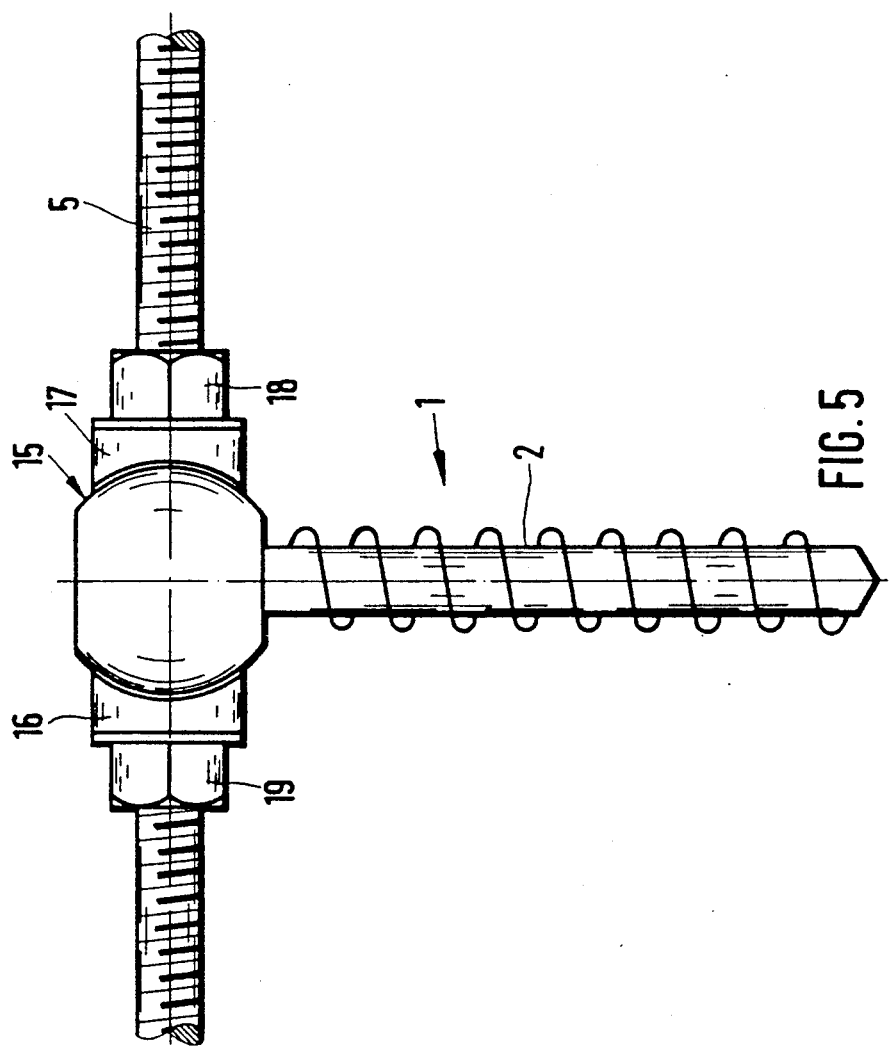

POSITIONING DEVICE

The invention relates to a positioning device for stabilizing segments of the spinal column, comprising a threaded shaft part and a receiver part for receiving a rod at the head side, wherein the rod and the receiver part are adapted to be rigidly connected with each other by means of two fixing members engaging the receiver part. Such devices are used for stabilizing the spinal column or for stabilizing a dummy between two adjacent vertebrae.

A positioning screw is disclosed in the DE-AS No. 26 49 042. The screw comprises a threaded shaft part and a receiver part rigidly provided at the head end of the threaded shaft part. The respective receiver parts comprise receiving slots. The lateral boundaries of the slots are formed by plane surfaces with concentric depressions. The engaging nuts have plane abutment surfaces with concentric collars. The collars engage the depressions and the plane surfaces of the nuts cooperate with the plane surfaces of the receiver part. It is thereby prevented that the rod disengages from the receiver part. Furthermore, the receiver rod is fixed in a position perpendicular to the axis of the receiver part. Pressure distributing plates are adapted in shape to the vertebrae and placed below the screw heads. A disadvantage of this solution is the difficulty to on the one hand tightly screw the screws into the vertebrae and on the other hand adjust the screws in two planes exactly such that the axes of the receiving slots in the receiver parts on top of each other are aligned such that the threaded rod may be passed through the receiving slots without placing stress on the screws. Already such an attempt requires a lot of time which is a great disadvantage for an operation at the spinal column. Moreover, it is nearly impossible to obtain such an exact alignment. As a result considerable shear forces act upon the threaded rods and thus the rods may even break in the later use after the operation or do not provide the desired stabilization. In addition, the required pressure distributing plates are additional movable parts and their mounting and handling renders the operation more difficult.

It is the object of the invention to provide a positioning device of the above-described kind which facilitates the mounting operation and at the same time reduces or avoids dangers in the later use.

This object is achieved by a positioning device of the above-described kind which is characterized by the features of the characterizing part of claim 1.

Further developments of the invention will stand out from a description of embodiments with reference to the drawings. In the drawings:

FIG. 3 represents a second embodiment in a view corresponding to the one of FIG. 1;

FIG. 4 represents the second embodiment in a view corresponding to that of FIG. 2;

FIG. 5 is a lateral view of a third embodiment; and

FIG. 6 represents the third embodiment in the view corresponding to that of FIG. 1.

Figures 1, 2:
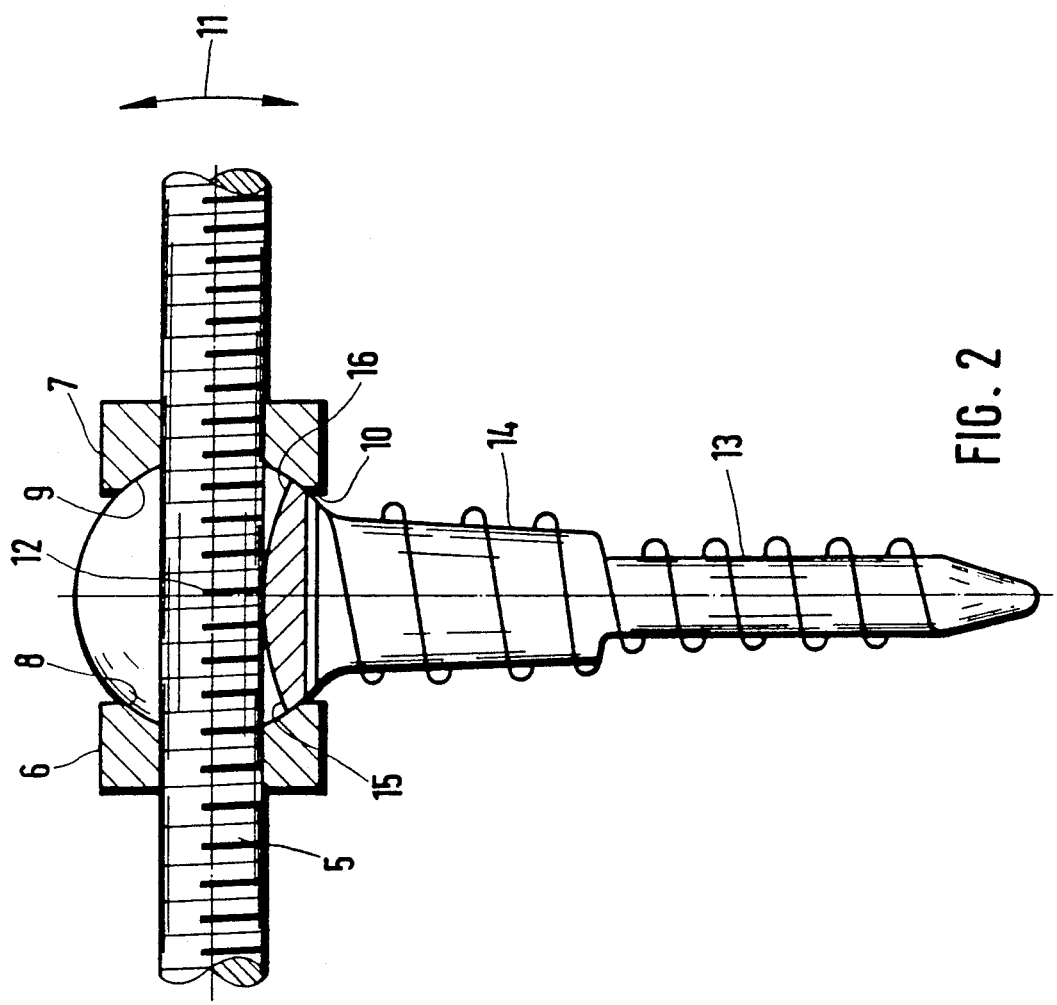
FIG. 1 is a lateral view of the positioning device in a direction perpendicular to the longitudinal axis of the rod.
FIG. 2 is a lateral view normally to the view of FIG. 1 with the fixing members and the receiver part being cut.

The positioning device comprises a positioning screw 1 with a threaded shaft part 2 and a receiver part 3.

The receiver part 3 comprises a spherical head which is provided with a slot 4 extending substantially perpendicular to the axis of the threaded shaft part 2. The slot receives a rod 5 which is formed as a threaded rod. Two nuts 6, 7 are provided for fixing the rod in the slot. The nuts 6, 7 are guided on the rod 5 and engage the exterior of the head.

The center plane of the slot coincides with the center of the spherical head. The slot extends into the head beyond the center of the spherical head by more than half a diameter of the rod such that it is possible to pivot or swing the rod with its center axis around the center of the sphere in a desired angular region in direction of the center plane of the slot.

The width of the slot 4 is selected larger than the diameter of the rod 5. This allows to also pivot or swing the rod with its center axis around the center of the spherical head in a direction perpendicular to the first mentioned pivot or swing direction within a predetermined angular region.

As best shown in FIG. 2, in the first embodiment the nuts 6, 7 have engagement surfaces at their sides facing the spherical head, the engagement surfaces being shaped as hollow spherical segment surfaces 8, 9. The radius of these surfaces is substantially equal to the radius of the spherical head such that the nuts contact all-over the wall of the spherical portion.

As best shown in FIG. 2, the nuts are designed such that there is a distance between their lower edge 10 and the adjacent portion of the threaded shaft part 2. In this manner a pivoting or swivelling action of the rod 5 in direction of the arrow 11 around the center 12 of the sphere is not restricted.

The threaded shaft part 2 has at its end opposite to the receiver part 3 a portion 13 with a first diameter. This portion extends over the major fraction of the length of the threaded shaft part. Between this portion and the receiver part 3 there is a further threaded portion 14 having a greater diameter or a greater thread, resp.

In operation, the positioning screw is first screwed into the vertebra or a dummy between two vertebrae. By providing the two portions 13 and 14 having threads of differing sizes, the positioning screw is fixed in such a tight manner that additional washers are no longer required. Subsequently the rod 5 is placed in the slot of the positioning screw and at the same time in the slots of the other positioning screws fixing the rod. Due to the described design of the slots the rod may be aligned also in a direction deviating from a direction which is perpendicular to the longitudinal direction of the threaded shaft parts. Subsequently the nuts 6, 7 are tightened such that they engage the receiver part in the manner shown in FIG. 2. The nuts are then tightened to such an extent that some kind of cold welding with the cooperating portions of the receiver part is generated.

In the above embodiment the slot has a plane bottom. Preferably, however, the slot bottom is lowered in longitudinal direction of the slot from the center thereof towards both outer ends 15, 16 in the manner shown in the Figures. Preferably the bottom has, in the plane including the slot axis, substantially a radius around a center which lies on the side of the spherical segment opposite to the center 13. It is thereby achieved that the rod 5 may be pivoted or swung around the center 12 of the spherical segment within a relatively large angle.

In the above-mentioned first embodiment the nuts directly engage the receiver part. In the embodiments shown in the FIGS. 3 and 4 the fixing members contacting the receiver part 3 are designed as disk-shaped intermediate pieces 6', 7' which are slidable back and forth on the rod 5 and which are engaged by nuts 20, 21 at the respective sides opposite to the receiver part 3. The shape of the intermediate parts 6', 7' on the side facing the receiver part 3 is identical to the one of the above-described nuts. In place of the internal thread a respective bore 22, 23 is provided and the diameter thereof is selected to allow the sliding on the rod 5.

The intermediate pieces 6', 7' have their inner surfaces cooperating with the receiver part 3 preferably roughened such that the tightened state of the nuts 20, 21 results in a fixed connection by cold welding between the intermediate pieces and the receiver part 3.

In operation it is proceeded in the same manner as in the first embodiment.

In the embodiment shown in the FIGS. 5 and 6 the receiver part 15 comprises a cylindrical head which has a slot 4 extending substantially perpendicular to the axis of the threaded shaft part 2. Again, the slot receives the rod 5 which is formed as a threaded rod. In order to fix the rod two intermediate members 16, 17 and nuts 18, 19 for engaging the intermediate members are provided which are guided on the rod 5 and engage the exterior of the head.

The slot 4 extends in a plane which is substantially perpendicular to the cylinder axis of the cylindrical head. Otherwise the design of the slot and its position is in conformity with the above-described embodiment.

The intermediate members 16, 17 have, on their sides facing the cylindrical head, engagement surfaces in the form of hollow cylindrical-shaped segments having a radius of curvature which corresponds substantially to the radius of curvature of the adjacent cylindrical segment surfaces such that the intermediate members contact the wall of the respective cylindrical segment-shaped portions of the receiver part 15. The intermediate members 16, 17 comprise bores which extend substantially through the center of the cylinder segment surfaces and perpendicular to the cylinder axis and which have a diameter selected such that the intermediate members are freely slidable on the rod 5.

As may be best seen from FIG. 3, the nuts 18, 19 engage the outward surfaces of the intermediate members 16, 17 opposite to the receiver part 15 such that a rigit connection between the rod 5 and the positioning screw 1 is obtained by means of the nuts 18, 19 and the intermediate members 16, 17.

In operation it is proceeded in the same manner as in the first embodiment.

We claim:

1. A positioning device for stabilizing spinal column segments, comprising, a position screw having a threaded shaft part and a receiver part, and a rod, said rod coupled to the receiver part of the positioning screw wherein the rod and the receiver part are adapted to be rigidly connectable to each other by means of two fixing members engaging the rod and the receiver part, further including the respective part of the receiver part forming the abutment for the fixing members is a sphere segment and that the engaging part of at least one of the fixing members comprises a hollow sphere segment shaped surface which is concentric to a bore of the fixing member receiving the rod.

2. The positioning device according to claim 1, further including both fixing members comprise respective hollow sphere segment shaped surfaces.

3. The positioning device according to claim 1 further including the radius of the hollow sphere segment shaped surface is substantially equal to the radius of the associated sphere segment.

4. A positioning device for stabilizing spinal column segments, comprising, a positioning screw having a threaded shaft part and a receiver part, the receiver part being cylindrically shaped and comprising a slot extending substantially perpendicular to the axis of said threaded shaft, and a rod, said rod coupled to the receiver part of the positioning screw by said slot wherein the rod and the receiver part are adapted to be rigidly connectable with each other by means of two nuts, a respective intermediate piece between the receiver part and the nuts, the intermediate piece having a surface facing the cylindrically-shaped receiver part in the form of a hollow cylindrical segment shaped surface corresponding substantially to the cylindrical shape of said receiving part.

5. The positioning device according to claim 2 further including the radius of the hollow sphere segment shaped surface is substantially equal to the radius of the associated sphere segment.

6. The positioning device according to one of the claims 1 to 4 or 5, further including the receiver part comprises a slot with a central plane which cuts through the center of the sphere segment or the longitudinal axis of the cylinder segment, resp.

7. The positioning device according to claim 6, the slot extends into the receiver part beyond the center of the receiver part by more than half a diameter of the rod.

8. The positioning device according to claim 7, further including the width of the slot is larger than the diameter of the rod.

9. The positioning device according claim 6,
further including the edge of at least one of the fixing members has a distance from the adjacent threaded shaft when the axis of the rod extends perpendicular to the axis of the threaded shaft.

10. The positioning device according to any of the claims 1 to 3 or 5,
further including the receiver part is sphere-shaped.

11. The positioning device according to any of the claims 1 to 4, or 5
further including the fixing members are formed as intermediate disks.

12. The positioning device according to any of the claims 1 to 4, or 5
further including the fixing members are formed as nuts.

13. The positioning device according to any of the claims 1 to 4, or 5
further including the threaded shaft comprises, at its end opposite to the receiver part, a portion having a first diameter and, adjacent thereto, a portion having a second diameter which is larger than the first diameter.

14. The positioning device according to claims 1 or 4, further including the receiver part comprising a slot, the plane of the slot extends substantially parallel to the longitudinal axis of the threaded shaft part.

15. The positioning device according to claims 1 or 4, further including the receiver part comprising a slot, the outer sides of the bottom of the slot are lowered in a longitudinal direction relative to the center of the slot, such that the rod may be pivoted around the center of the sphere segment or the cylindrical segment respectively.

* * * * *